(12) United States Patent
Barak

(10) Patent No.: US 10,959,668 B2
(45) Date of Patent: *Mar. 30, 2021

(54) SYSTEM AND METHOD FOR DETERMINING USER'S DEEP VEIN THROMBOSIS PREVENTION AND DIAGNOSIS SYSTEM UTILIZATION COMPLIANCE

(71) Applicant: Zimmer Dental Ltd., Rosh Haayin (IL)

(72) Inventor: Jacob Barak, Oranit (IL)

(73) Assignee: Zimmer Dental Ltd., Rosh Haayin (IL)

( * ) Notice: Subject to any disclaimer, the term of this patent is extended or adjusted under 35 U.S.C. 154(b) by 57 days.

This patent is subject to a terminal disclaimer.

(21) Appl. No.: 16/251,922

(22) Filed: Jan. 18, 2019

(65) Prior Publication Data

US 2019/0150830 A1    May 23, 2019

Related U.S. Application Data

(63) Continuation of application No. 14/818,719, filed on Aug. 5, 2015, now Pat. No. 10,226,211.

(Continued)

(51) Int. Cl.
| | |
|---|---|
| *A61B 5/00* | (2006.01) |
| *A61H 9/00* | (2006.01) |
| *A61B 5/0205* | (2006.01) |

(52) U.S. Cl.
CPC .......... *A61B 5/4833* (2013.01); *A61B 5/0205* (2013.01); *A61B 5/4519* (2013.01);
(Continued)

(58) Field of Classification Search
CPC ............ A61B 5/021–0295; A61H 9/005–0092
See application file for complete search history.

(56) References Cited

U.S. PATENT DOCUMENTS

| | | | |
|---|---|---|---|
| 6,387,065 B1 | 5/2002 | Tumey | |
| 7,637,879 B2 * | 12/2009 | Barak | ................. A61H 9/0078 601/149 |

(Continued)

FOREIGN PATENT DOCUMENTS

WO    WO-2014066077 A1    5/2014

OTHER PUBLICATIONS

"U.S. Appl. No. 14/818,719, Non Final Office Action dated Mar. 14, 2018", 11 pgs.

(Continued)

*Primary Examiner* — Nyca T Nguyen
(74) *Attorney, Agent, or Firm* — Schwegman Lundberg & Woessner, P.A

(57) ABSTRACT

A system and method determines a user's compliance with a prescribed therapeutic pneumatic compression treatment by applying external pressure to a body limb using a pneumatic compression sleeve having a pneumatically fillable cell; measuring pneumatic pressure within the pneumatically fillable cell; generating a pressure signal corresponding to the measured pneumatic pressure; determining biological events associated with the user based upon the pressure signal; generating a positive detection signal for each determined biological event associated with the user; and determining a user's compliance with a prescribed therapeutic pneumatic compression treatment when a predetermined number of positive detection signals have been generated within a predetermined time interval.

17 Claims, 10 Drawing Sheets

Related U.S. Application Data

(60) Provisional application No. 62/062,781, filed on Oct. 11, 2014.

(52) U.S. Cl.
CPC .......... *A61B 5/4848* (2013.01); *A61B 5/4884* (2013.01); *A61B 5/7278* (2013.01); *A61B 5/7282* (2013.01); *A61H 9/0078* (2013.01); *A61B 5/6828* (2013.01); *A61H 2201/164* (2013.01); *A61H 2201/165* (2013.01); *A61H 2201/1635* (2013.01); *A61H 2201/5002* (2013.01); *A61H 2201/5007* (2013.01); *A61H 2201/5043* (2013.01); *A61H 2201/5071* (2013.01); *A61H 2201/5097* (2013.01); *A61H 2209/00* (2013.01); *A61H 2230/06* (2013.01); *A61H 2230/42* (2013.01); *A61H 2230/60* (2013.01)

(56) References Cited

U.S. PATENT DOCUMENTS

| | | | | |
|---|---|---|---|---|
| 8,597,194 | B2* | 12/2013 | Barak | A61B 5/02007 600/485 |
| 10,226,211 | B2 | 3/2019 | Barak | |
| 2003/0078528 | A1 | 4/2003 | Rahman et al. | |
| 2003/0095263 | A1* | 5/2003 | Varshneya | A61B 5/113 356/477 |
| 2003/0204134 | A1* | 10/2003 | Nunome | A61B 5/14551 600/324 |
| 2005/0107725 | A1* | 5/2005 | Wild | A61H 9/0078 601/152 |
| 2005/0119833 | A1* | 6/2005 | Nanikashvili | A61B 5/1123 702/19 |
| 2005/0159690 | A1* | 7/2005 | Barak | A61H 9/0078 601/149 |
| 2006/0167390 | A1* | 7/2006 | Hui | A61H 9/0078 601/152 |
| 2008/0103397 | A1* | 5/2008 | Barak | A61H 9/0078 600/492 |
| 2008/0294021 | A1* | 11/2008 | Lin | A61B 5/022 600/301 |
| 2009/0024062 | A1 | 1/2009 | Einarsson | |
| 2009/0036790 | A1* | 2/2009 | Landesberg | A61B 5/062 600/529 |
| 2010/0094140 | A1* | 4/2010 | Pranevicius | A61B 5/021 600/485 |
| 2010/0292619 | A1* | 11/2010 | Redington | A61H 9/0078 601/84 |
| 2011/0066007 | A1* | 3/2011 | Banet | A61B 5/1116 600/301 |
| 2011/0066044 | A1* | 3/2011 | Moon | A61B 5/02125 600/485 |
| 2011/0152651 | A1* | 6/2011 | Berkow | A61B 5/02416 600/324 |
| 2011/0190675 | A1* | 8/2011 | Vess | A61H 9/0092 601/152 |
| 2012/0083712 | A1 | 4/2012 | Watson et al. | |
| 2013/0231596 | A1* | 9/2013 | Hornbach | G16H 40/63 601/150 |
| 2013/0331747 | A1* | 12/2013 | Helgeson | A61H 23/04 601/48 |
| 2014/0031730 | A1* | 1/2014 | Hornbach | A61B 5/02141 601/148 |
| 2014/0070957 | A1 | 3/2014 | Longinotti-Buitoni et al. | |
| 2014/0329214 | A1* | 11/2014 | Bitoun | G16H 40/63 434/262 |
| 2015/0250426 | A1* | 9/2015 | Muehlsteff | A61B 5/0402 600/301 |
| 2016/0100793 | A1* | 4/2016 | Barak | A61B 5/4519 600/301 |
| 2016/0166464 | A1* | 6/2016 | Douglas | A61H 9/0078 601/148 |
| 2016/0242656 | A1* | 8/2016 | Jackson | A61B 5/6825 |
| 2018/0000651 | A1* | 1/2018 | Pan | A61H 9/0078 |

OTHER PUBLICATIONS

"U.S. Appl. No. 14/818,719, Notice of Allowance dated Oct. 22, 2018", 12 pgs.

"U.S. Appl. No. 14/818,719, Response filed Jun. 14, 2018 to Non Final Office Action dated Mar. 14, 2018", 8 pgs.

"International Application Serial No. PCT/IL2015/050852, International Preliminary Report on Patentability dated Apr. 20, 2017", 9 pgs.

"International Application Serial No. PCT/IL2015/050852, International Search Report dated Feb. 9, 2016", 5 pgs.

"International Application Serial No. PCT/IL2015/050852, Written Opinion dated Feb. 9, 2016", 7 pgs.

\* cited by examiner

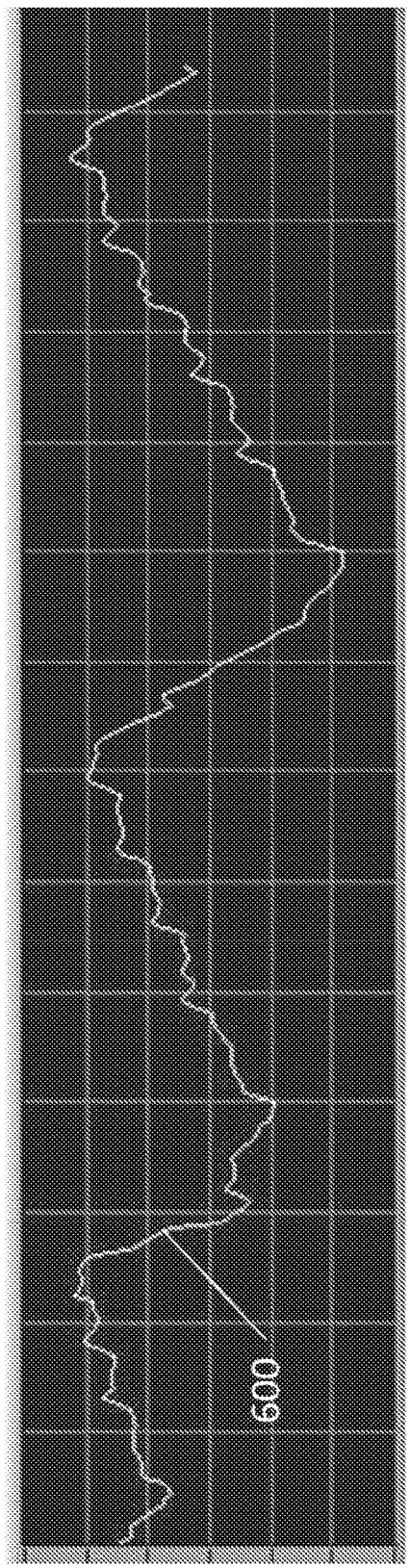
FIGURE 9
FIGURE 10

FIGURE 13

SYSTEM AND METHOD FOR DETERMINING USER'S DEEP VEIN THROMBOSIS PREVENTION AND DIAGNOSIS SYSTEM UTILIZATION COMPLIANCE

PRIORITY INFORMATION

This application claims priority under 35 U.S.C. § 119 to U.S. Provisional Patent Application Ser. No. 62/062,871, which was filed on Oct. 11, 2014. The entire content of U.S. Provisional Patent Application Ser. No. 62/062,871, which was filed on Oct. 11, 2014, is hereby incorporated by reference.

BACKGROUND

Various conventional compression devices are known for applying compressive pressure to a patient's limb. These types of devices are used to assist in a large number of medical indications, mainly the prevention of deep vein thrombosis (DVT), vascular disorders, reduction of edemas, and the healing of wounds.

Although showing high clinical efficacy in clinical studies in treating the above conditions, compression devices are only effective is the user utilizes the compression device in compliance with the prescribed treatment.

For example, the prescribed treatment may be utilizing the compression device for a predetermined amount of time during the day or utilizing the compression device a predetermined number of times for a predetermined amount of time during the day. If the user is not compliant with the prescribed treatment, the practitioner cannot readily determine is the compression device is non-effective unless the practitioner is aware of the user's non-compliance.

Various clinical studies have shown that daily compliance of compression systems is less than 50% resulting in far below expectation clinical outcomes compared to a continuous treatment. Such non-compliance by the user can have negative consequences.

For example, deep vein thrombosis carries the short-term risk of pulmonary embolism and death and the long term risk of chronic venous insufficiency, causing disabling symptoms of swelling, chronic pain, and skin ulceration (post thrombotic syndrome). Both pulmonary embolism and post-thrombotic syndrome may develop after symptomatic or asymptomatic, proximal or distal deep vein thrombosis events.

As disclosed in U.S. Pat. No. 8,597,194, deep vein thrombosis can be detected and prevented by a compression device. The entire contents of U.S. Pat. No. 8,597,194 are hereby incorporated by reference.

However, if the user is not utilizing the compression device as prescribed, deep vein thrombosis may not be detected or prevented, thus, determining compliance by the user enables the successful utilization of a compression device.

Therefore, it is desirable to provide a compression device that will detect a user's compliance status in the utilization of the compression device.

Furthermore, it is desirable to provide a compression device that will detect a user's compliance status in the utilization of the compression device and store the compliance data for review by a competent medical practitioner.

Moreover, it is desirable to provide a compression device that will detect a user's compliance status in the utilization of the compression device and communicate the compliance data to a monitoring service or competent medical practitioner.

Also, it is desirable to provide a compression device that will detect, in real time, a user's compliance status in the utilization of the compression device and provide an alert or notice to the user of the compliance status.

BRIEF DESCRIPTION OF THE DRAWINGS

The drawings are only for purposes of illustrating embodiments and are not to be construed as limiting, wherein:

FIG. 9 shows a graph showing a signal representing respiratory activity as measured by pressure sensors;

FIG. 10 shows a graph showing changes in the signal of FIG. 9 that represents measurements of compliance;

FIG. 13 shows a display screen of a compliance monitoring device.

DETAILED DESCRIPTION

Figure 1:
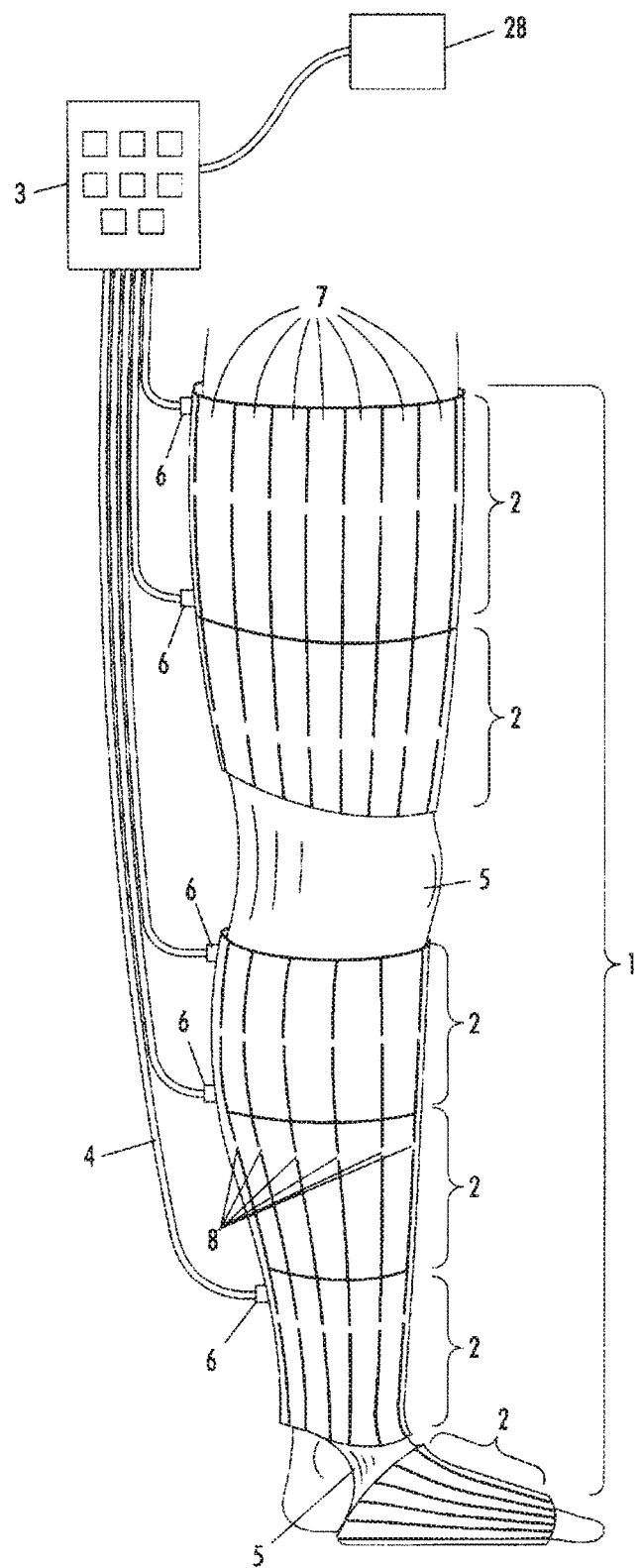
FIG. 1 is an illustration showing a massage/diagnostic sleeve in use on the leg of a patient.

For a general understanding, reference is made to the drawings. In the drawings, like reference have been used throughout to designate identical or equivalent elements. It is also noted that the various drawings may not have been drawn to scale and that certain regions may have been purposely drawn disproportionately so that the features and concepts could be properly illustrated.

In the following descriptions, the concepts will be described with respect to use on a leg of an individual. However, it is to be understood that the concepts are also extended to use on any body limb such as an arm, a foot, a part of a leg, arm, or foot, and may be used on two or more limbs simultaneously.

Moreover, although the concepts will be described in conjunction with a portable pneumatic compression system console or small pneumatic compression system console wherein the medium used to provide compression is realized by pressurized air, the concepts can be used with any compression system wherein the medium used to provide compression can be realized by a liquid, fluid, gas, or any other mechanical means.

The descriptions below relate to medical devices for applying pressure to a region of a body surface. More particularly, the descriptions below relate to medical devices that use a pressure sleeve to apply pressure to a region of a body surface for deep vein thrombosis therapeutic and diagnostic purposes.

It is noted that the entire contents of U.S. Pat. Nos. 7,063,676; 7,591,796; and 7,637,879 are hereby incorporated by reference.

In FIG. 1, an exemplary embodiment of a pressure massage/diagnostic sleeve 1 is illustrated. The pressure massage/diagnostic sleeve 1 has an inner and outer surface composed of a durable flexible material and is divided into a plurality of cells 2 along its length and each cell is connected to the control unit 3 by a separate tube collectively labeled 4 in FIG. 1. Sections of the pressure massage/diagnostic sleeve may be of non-inflatable elastic material 5, for example around the knee and ankle.

As illustrated in FIG. 1, each cell has a fluid inlet opening 6 to which a hose 4 from the control unit 3 is attached. The control unit 3 contains a compressor capable of compressing and pumping ambient air into one or more selected cells in the pressure massage/diagnostic sleeve via the hoses 4. It is noted that the console may also include a compression system wherein the medium used to provide compression can be realized by a liquid, fluid, gas, or other mechanical means.

The control unit 3 allows a temporo-spatial regime of inflation and deflation of the cells to be selected, e.g. a regime which generates peristaltic contractions of the pressure massage/diagnostic sleeve so as to force fluids inside the limb towards the proximal end of the limb, or a regime which enhances the flow of the venous blood in the limb.

The cells may be subdivided into a plurality of intra-cell compartments 7. The intra-cell compartments 7 are formed, for example, by welding the inner and outer shells of the pressure massage/diagnostic sleeve along the boundaries of the intra-cell compartments. The intra-cell compartments 7 in a given cell are confluent due to openings 8 between adjacent intra-cell compartments 7 so that all the intra-cell compartments 7 in the cell are inflated or deflated essentially simultaneously.

Figure 2:
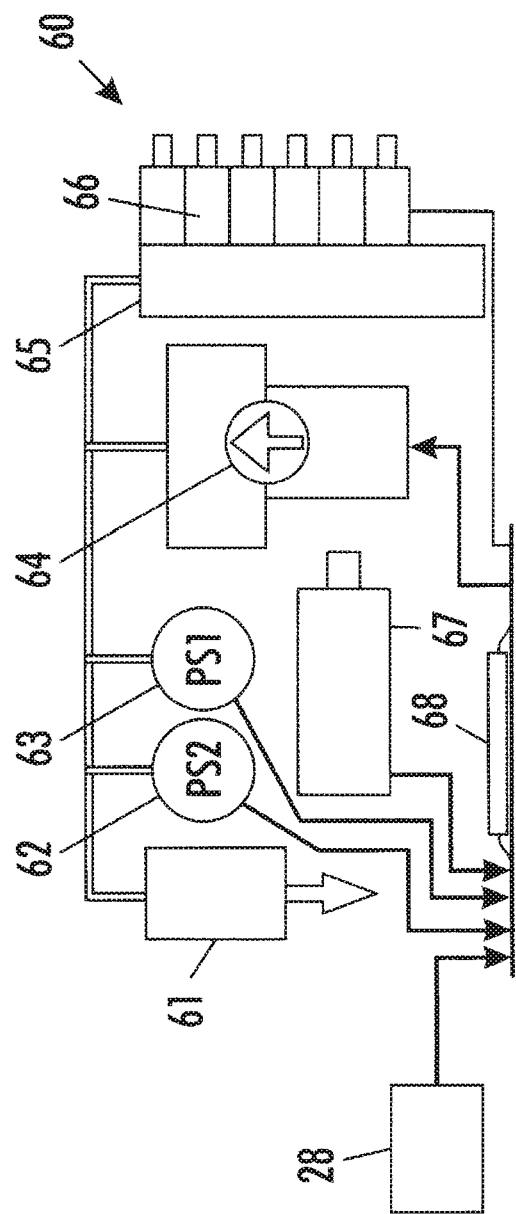
FIG. 2 is a schematic block diagram of a compression unit.

FIG. 2 is a schematic block diagram of a compression unit 60. It will be appreciated that the thick interconnecting lines represent a pneumatic connection or multiple pneumatic connections, while the thin interconnecting lines represent an electrical connection or multiple electrical connections. The compression unit 60 may include an independent source of energy, such as a rechargeable battery pack 67, which enables the pneumatic device operation without a fixed connection to a main power outlet. The batteries can be bypassed and the device is able to operate for longer times, and the batteries can be recharged at the same time, while it is connected to the main power supply with the aid of a charger.

A source of compressed air, such as a compressor 64, is powered by the batteries or the main electrical outlet, and connected to the pressure massage/diagnostic sleeve or sleeves by pneumatic conduits. A control unit 68 is adapted to receive inputs from the operator and from pressure sensors 62 and 63.

The control unit serves to read and control the operation of the compressor 64 and to control the cyclic inflating and deflating of the pressure massage/diagnostic sleeve.

The control unit also controls the operation of solenoid valves 66, which receive and distribute the flow to the different cells of the pressure massage/diagnostic sleeve with the aid of a manifold 65, to enable the sequential inflating and deflating of the multi-segmented pressure massage/diagnostic sleeve's cells.

It is noted that the compressor 64 may be housed within the control unit or may be housed separately. It is noted that pressure sensors 62 and 63 may have individual pneumatic connections with the manifold 65.

Alternatively, both the hardware and software can enable the operation of the device from an external pressurized air and power sources. In some hospitals, the source of pressurized air can be the central source of pressure-regulated supply that has wall outlets adjacent to the power outlets or that both the external power and pump sources could be an integral part of the patient's bed.

The use of miniaturized components like the compressor 64 and solenoid valves 66, together with the miniature accessories, results in small power consumption that enables the operation of the pneumatic device on batteries, while maintaining small dimensions and lightweight of the operating unit. The use of a pressure massage/diagnostic sleeve with a small-inflated volume can also improve the obtained results of the operation unit for better clinical operation and results.

The system applies cyclic sequential pressure on a body's legs or arms. The cyclic sequential pressure is applied on the treated parts of the body by inflating and deflating each cell of the pressure massage/diagnostic sleeve at a predefined timing. While being inflated, the multi-chambered segmented sleeve should be encircling the part of leg to be treated. While the pressure massage/diagnostic sleeve is inflated, a local pressure is applied at the contact area between the pressure massage/diagnostic sleeve and the body.

The control unit 68, which can be software based, controls the operation of the compressor 64 and solenoid valves 66. The control unit can be programmed to achieve any desired inflating, deflating, and/or recording sequence and timing including delay intervals, in accordance with clinical application.

As noted above, compliant use of a compression device is desired so that the user (patient) can realize the therapeutic benefits of the compression treatment. Also, it is desirable that a care provider and/or medical practitioner can readily determine if the user has been compliant with their use of the compression device.

Figure 3:
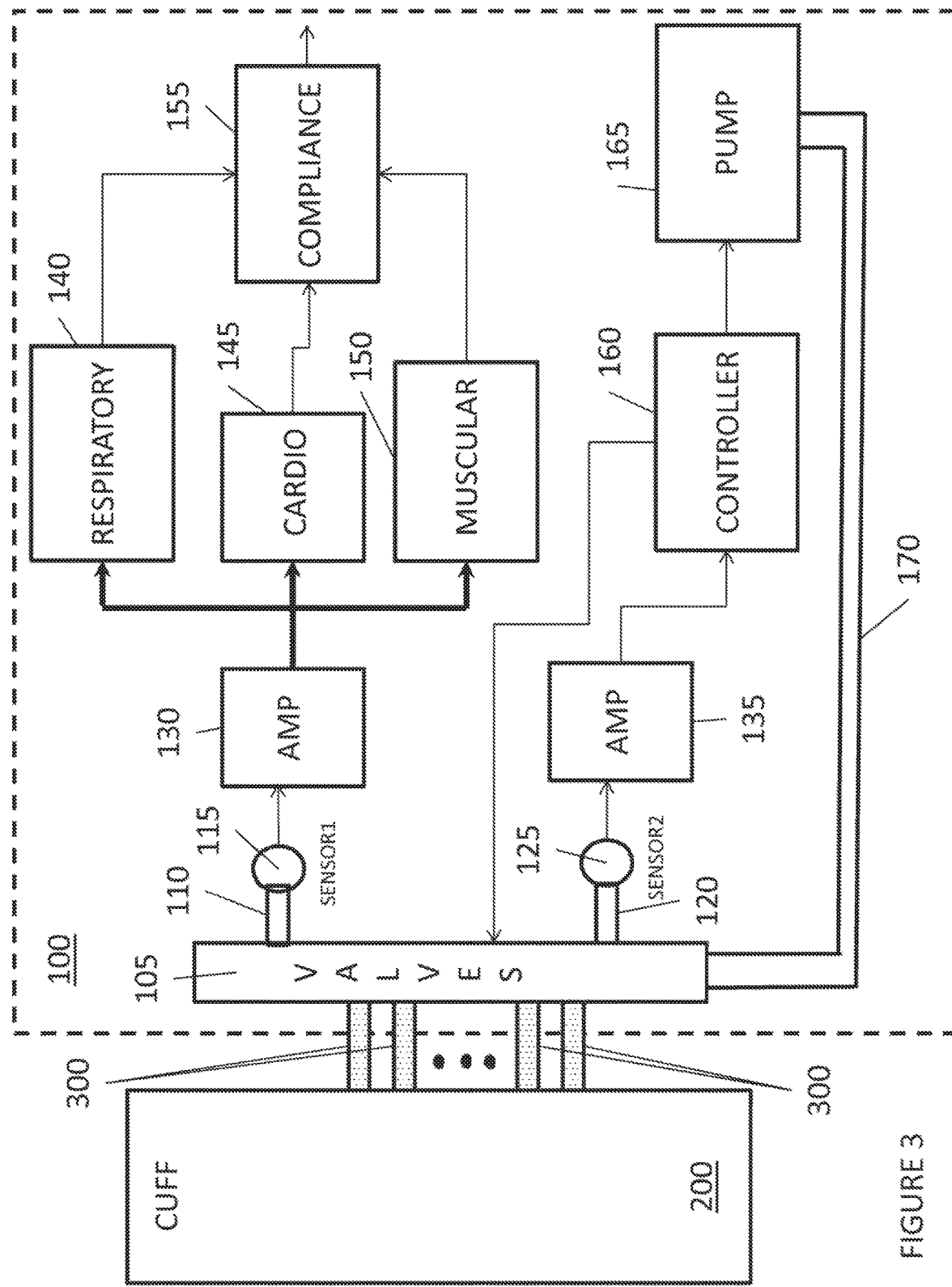
FIG. 3 is a schematic block diagram of a compliance monitoring compression system.

FIG. 3 illustrates a compression device with a compliance measuring feature. As illustrated in FIG. 3, a compression console 100 includes a pump 165 for pumping fluids, through a conduit 170, to a set of valves 105.

The operations pump 165 is controlled by a controller 160 based upon predetermined therapeutic treatments.

The set of valves 105 are controlled by controller 160 to establish which conduits 300 receive the fluid from conduit 170 to enable the cuff 200 or portions thereof to compress a body limb.

The set of valves 105 are also controlled by controller 160 to establish which conduits 300 are connected to pressure sensors 115 and 125 to measure pressure or pressure fluctuations at certain portions of the cuff 200. The pressure or pressure fluctuations may represent certain biological events, such as muscle activity, pulse, respiration, venous phasic flow, etc.

In addition, the set of valves 105 are also controlled by controller 160 to enable, through conduits 300, fluid evacuation of the cuff 200.

A more detail discussion of valve control is set forth in U.S. Pat. Nos. 7,063,676 and 7,591,796, which contents are hereby incorporated by reference.

The operations pump 165 is controlled by a controller 160 based upon predetermined therapeutic treatments.

For example, as discussed in U.S. Pat. No. 7,637,879, which content is hereby incorporated by reference, pressure or pressure fluctuations in the cuff 200 are measured by a pressure sensor 125 and amplified by amplifier 135, and based upon these measurements (amplified signals), the controller 165 may control the pump 160 to provide the proper compression; e.g., compression in phase with a venous phasic flow.

In FIG. 3, sensor 125 measures certain biological events, based upon pressure or pressure fluctuations measurements, which the controller 165 uses to control the pump 160.

In this embodiment, sensor 125 is utilized to measure higher pressure range; e.g., the pressure sensor 125 may be utilized to measure pressures in the range of 0-375 mmHg; i.e., compression of the cuff 200. The amplifier 135 may amplify the signal by $0.23*10^6$.

It is noted that the amplifier 135 may be optional is the strength from the sensor 125 is strong enough to process by the controller 165.

FIG. 3 also illustrates a compliance system that measures the user compliance with respect to utilizing the compression device. As illustrated in FIG. 3, the compression console 100 includes a sensor 115, which measures pressure or pressure fluctuations in the cuff 200.

In this embodiment, sensor 115 is utilized to measure a lower pressure range; e.g., the pressure sensor 115 may be utilized to measure pressures in the range of 0-75 mmHg; i.e., measuring muscle activity, pulse, and/or respiration.

An amplifier 130 amplifies the signal and outputs the signal to a respiratory measuring device 140, a cardio measuring device 145, and a muscular activity measuring device 150. The amplifier 130 may amplify the signal by $1.5*10^6$.

It is noted that the amplifier 130 may be optional is the strength from the sensor 115 is strong enough to process by the respiratory measuring device 140, the cardio measuring device 145, and the muscular activity measuring device 150.

It is noted that although FIG. 3 illustrates that the respiratory measuring device 140, the cardio measuring device 145, and the muscular activity measuring device 150 are connected in parallel, these devices can operate in a serial fashion.

It is further noted that although FIG. 3 illustrates that the respiratory measuring device 140, the cardio measuring device 145, and the muscular activity measuring device 150 are separate devices, the functions of these devices, as described below, may be realized by a processor executing an application, an application specific integrated circuit, and/or a combination of hardware, firmware, and/or software.

The respiratory measuring device 140 monitors the amplified signal from the amplifier 130 to detect signals representing respiration (breathe). An example of an amplified signal that shows respiration is FIG. 9.

As illustrated in FIG. 9, an amplified signal 600 represents a user (patient) using the compression device while resting or sleeping on their back. The respiratory measuring device 140 detects respiration (breathe) when the difference (610) between a signal peak and a signal minimum is greater than a predetermined threshold. For example, if the difference (610) between a signal peak and a signal minimum represents a difference greater than 0.1 mmHg or approximately 5 mV, respiration (breathe) is detected.

The cardio measuring device 145 monitors the amplified signal from the amplifier 130 to detect signals representing heart functions (pulse). An example of an amplified signal that shows heart functions (pulse) is FIG. 7.

Figure 7:
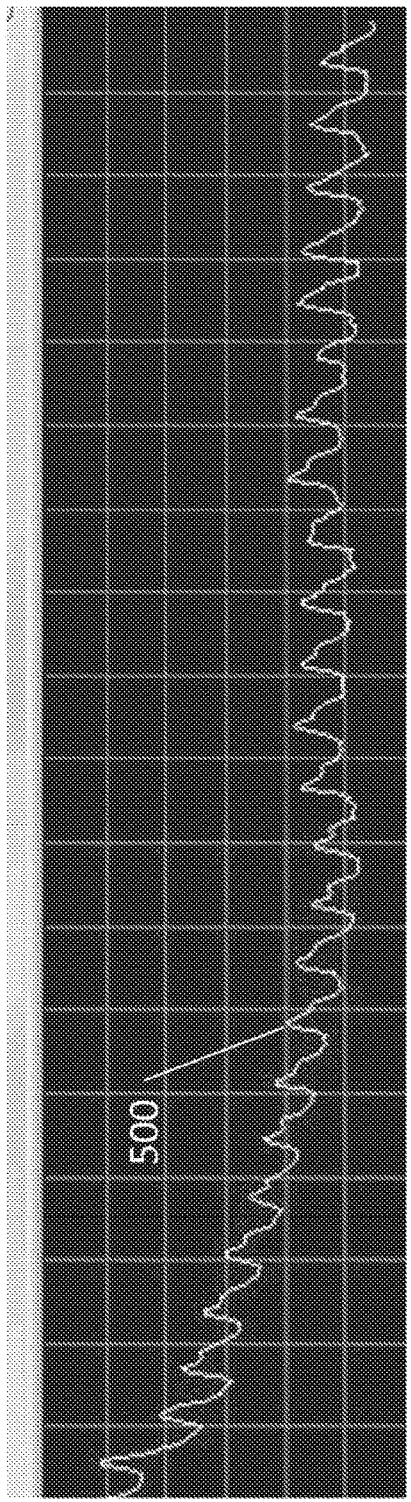
FIG. 7 shows a graph showing a signal representing cardio activity as measured by pressure sensors.
Figure 8:
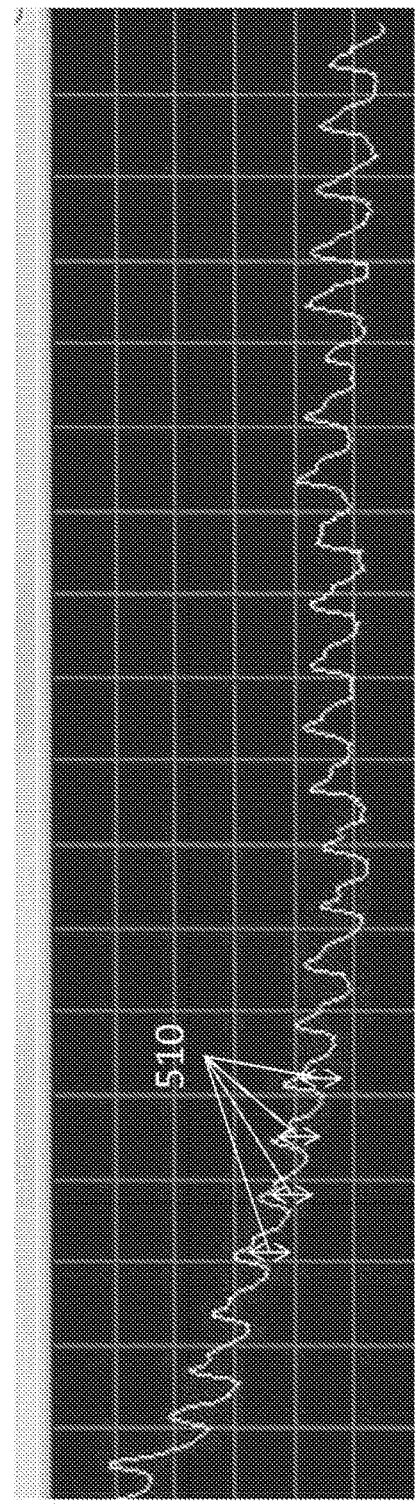
FIG. 8 shows a graph showing changes in the signal of FIG. 7 that represents measurements of compliance.

As illustrated in FIG. 7, an amplified signal 500 represents a user (patient) using the compression device while resting or sleeping on their side (making it harder to detect respiration) or while holding their breathe. The cardio measuring device 145 detects heart functions (pulse) when the difference (510) between a signal peak and a signal minimum is greater than a predetermined threshold. For example, if the difference (510) between a signal peak and a signal minimum represents a difference greater than 0.1 mmHg or approximately 5 mV, a heart function (pulse) is detected.

The muscular activity measuring device 150 monitors the amplified signal from the amplifier 130 to detect signals representing muscular activity. An example of an amplified signal that shows muscular activity is FIG. 5.

Figure 5:
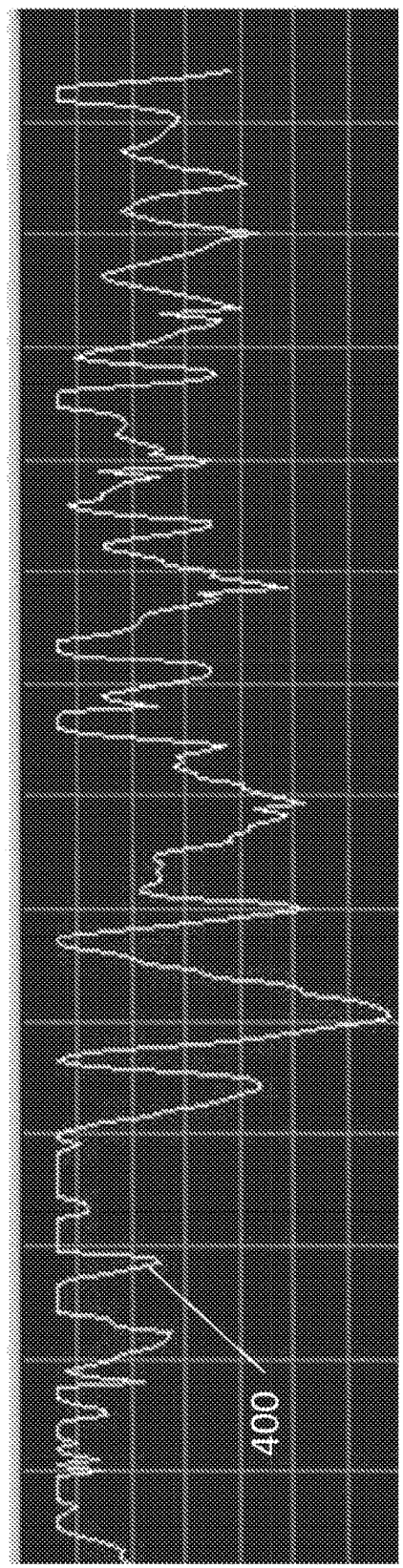
FIG. 5 shows a graph showing a signal representing muscle activity as measured by pressure sensors.
Figure 6:
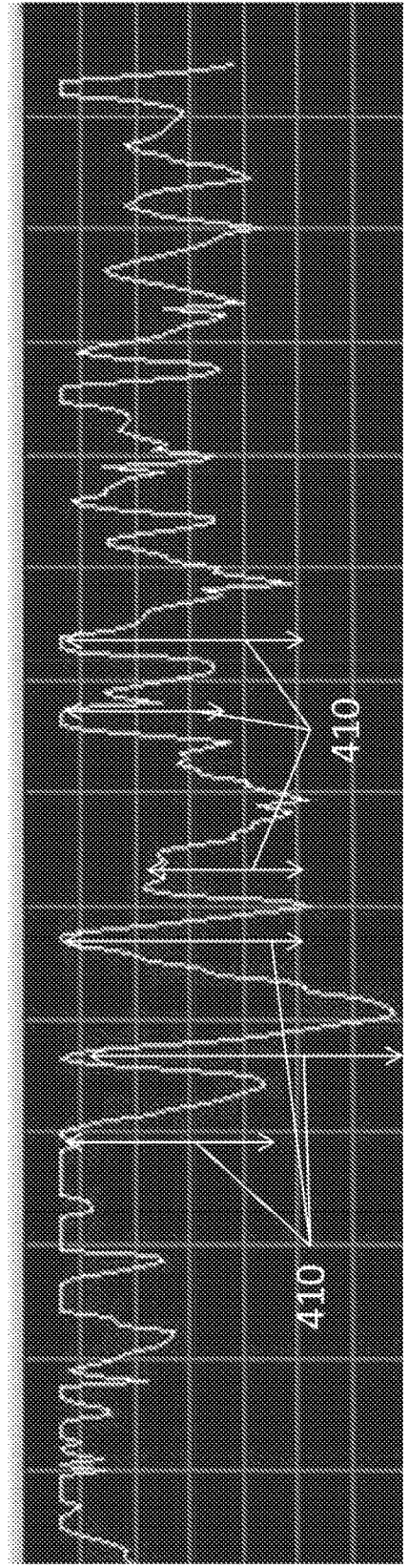
FIG. 6 shows a graph showing changes in the signal of FIG. 6 that represents measurements of compliance.

As illustrated in FIG. 5, an amplified signal 400 represents a user (patient) using the compression device while engaging in muscular activity, such as walking, etc. The muscular activity measuring device 150 detects muscular activity when the difference (410) between a signal peak and a signal minimum is greater than a predetermined threshold. For example, if the difference (510) between a signal peak and a signal minimum represents a difference greater than 0.1 mmHg or approximately 5 mV, muscular activity is detected.

It is noted that when a user (patient) using the compression device is walking, the muscle generated signals would mask all other signals since the muscle generated signals are much stronger than the pulse or breathe signals.

It is further noted that a predetermined time interval may be required between measured signals; e.g., a two second interval between signals; to avoid or filter out signals associated with vibrations caused by a nearby electronic appliance.

It is also noted that the respiratory measuring device 140, the cardio measuring device 145, and the muscular activity measuring device 150, each contain sampling and/or filtering functionality to process the gross signal received from the amplifier 130.

For example, the respiratory measuring device 140 may include sampling and/or filtering functionality which would process the gross signal received from the amplifier 130 so that a periodic signal, having a cycle representative of the patient's normal respiration rate or a predetermined respiration rate, would be realized. This periodic signal, as illustrated in FIG. 9, can be further analyzed to determine the difference between a signal peak and a signal minimum (610) would be effective in detecting respiration. Such filtering and/or sampling techniques are well-known in the art.

Moreover, for example, the muscular activity measuring device 150 may include sampling and/or filtering functionality which would process the gross signal received from the amplifier 130 so that a periodic signal, having a cycle representative of the patient's normal pulse rate or a predetermined pulse rate, would be realized. This periodic signal, as illustrated in FIG. 5, can be further analyzed to determine the difference between a signal peak and a signal minimum (410) would be effective in detecting muscular activity. Such filtering and/or sampling techniques are well-known in the art.

Lastly, for example, the cardio measuring device 145 may include sampling and/or filtering functionality which would process the gross signal received from the amplifier 130 so that a periodic signal, having a cycle representative of the patient's normal pulse rate or a predetermined pulse rate, would be realized. This periodic signal, as illustrated in FIG. 7, can be further analyzed to determine the difference between a signal peak and a signal minimum (510) would be effective in detecting cardio activity. Such filtering and/or sampling techniques are well-known in the art.

As illustrated in FIG. 3, the respiratory measuring device 140, the cardio measuring device 145, and the muscular activity measuring device 150 output the detection signals (positive signals indicating the measured activity) to the compliance device 155.

The compliance device 155 receives the various detection signals and determines if the user is in compliance with the prescribed usage of the compression device.

To determine compliance, the compliance device 155 determines if a predetermined number of detection signals are received within a predetermined window of time.

For example, the compliance device 155 may make a positive compliance determination if five positive detection signals are received during a five minute interval. More specifically, if the compliance device 155 receives five positive detection signals in a five minute window, the compliance device 155 determines that the user's utilization of the compression device is in compliance.

It is noted that the five positive detection signals may not be all from the same source (the respiratory measuring device 140, the cardio measuring device 145, or the muscular activity measuring device 150). For example, the five detection signals can be all pulse detection signals, all breathe detection signals, or all muscular activity detection signals, or any combination thereof; e.g., two breathe detection signals, two pulse detection signals, and one muscular activity detection signal, etc.

It is noted that if only a single cuff is utilized in the therapeutic treatment, each detected positive detection signal may counted as two positive detection signal signals in the compliance analysis.

Figure 4:
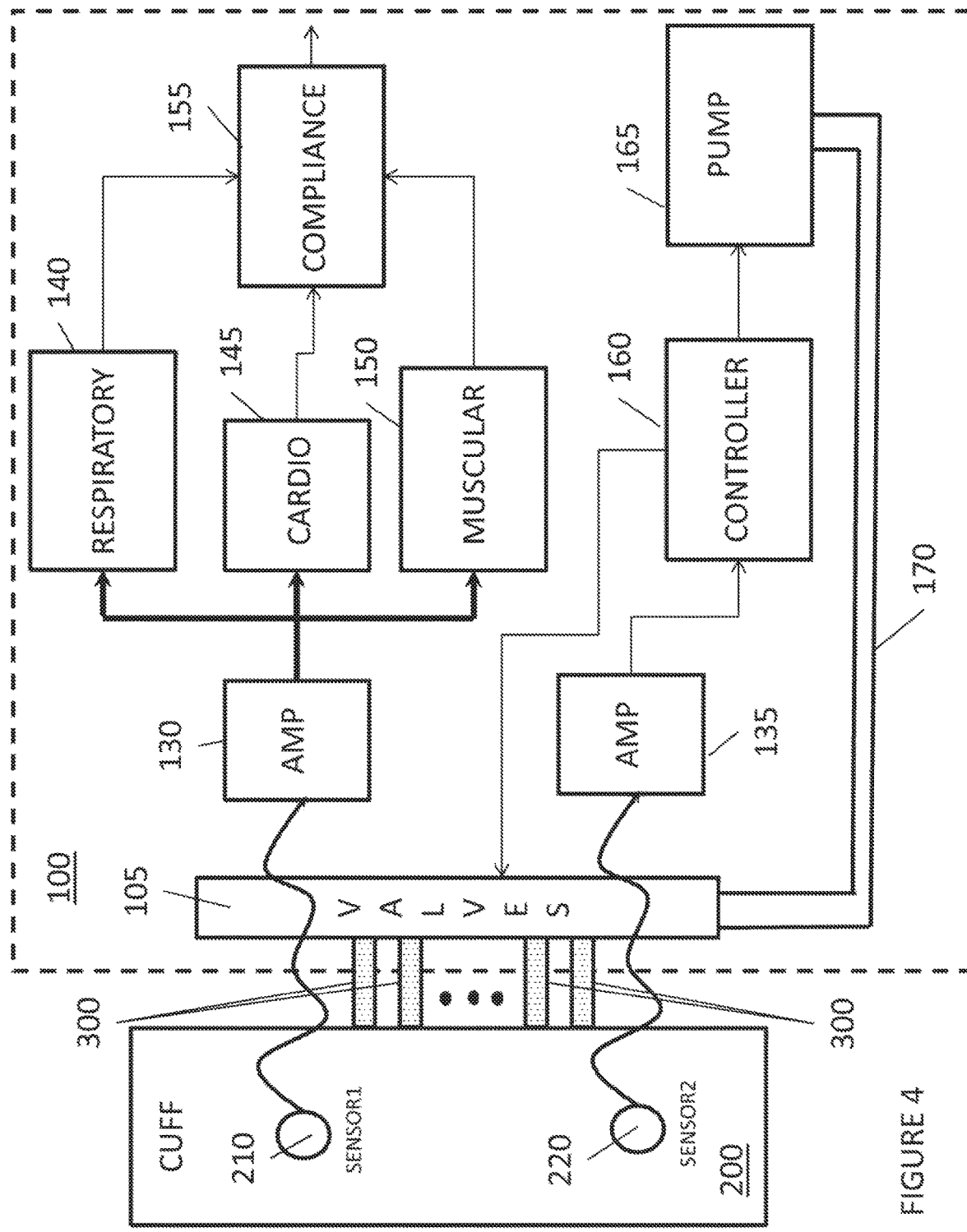
FIG. 4 is another schematic block diagram of a compliance monitoring compression system.

FIG. 4 illustrates a compression device with a compliance measuring feature. As illustrated in FIG. 4, a compression console 100 includes a pump 165 for pumping fluids, through a conduit 170, to a set of valves 105.

The operations pump 165 is controlled by a controller 160 based upon predetermined therapeutic treatments.

The set of valves 105 are controlled by controller 160 to establish which conduits 300 receive the fluid from conduit 170 to enable the cuff 200 or portions thereof to compress a body limb.

In addition, the set of valves 105 are also controlled by controller 160 to enable, through conduits 300, fluid evacuation of the cuff 200.

A more detail discussion of valve control is set forth in U.S. Pat. Nos. 7,063,676 and 7,591,796, which contents are hereby incorporated by reference.

The operations pump 165 is controlled by a controller 160 based upon predetermined therapeutic treatments.

For example, as discussed in U.S. Pat. No. 7,637,879, which content is hereby incorporated by reference, pressure or pressure fluctuations in the cuff 200 are measured by a pressure sensor 125 and amplified by amplifier 135, and based upon these measurements (amplified signals), the controller 165 may control the pump 160 to provide the proper compression; e.g., compression in phase with a venous phasic flow.

In FIG. 4, sensor 220 is located on the cuff 200 and measures certain biological events, based upon pressure or pressure fluctuations measurements, which the controller 165 uses to control the pump 160. The sensor 220 communicates to the amplifier 135 over a wire or wirelessly.

In this embodiment, sensor 220 is utilized to measure higher pressure range; e.g., the pressure sensor 220 may be utilized to measure pressures in the range of 0-375 mmHg; i.e., compression of the cuff 200. The amplifier 135 may amplify the signal by $0.23*10^6$.

It is noted that the amplifier 135 may be optional is the strength from the sensor 220 is strong enough to process by the controller 165.

FIG. 4 also illustrates a compliance system that measures the user compliance with respect to utilizing the compression device. As illustrated in FIG. 4, the cuff 200 includes a sensor 210, which measures pressure or pressure fluctuations in the cuff 200. The sensor 210 communicates to the amplifier 130 over a wire or wirelessly.

In this embodiment, sensor 210 is utilized to measure a lower pressure range; e.g., the pressure sensor 210 may be utilized to measure pressures in the range of 0-75 mmHg; i.e., measuring muscle activity, pulse, and/or respiration.

An amplifier 130 amplifies the signal and outputs the signal to a respiratory measuring device 140, a cardio measuring device 145, and a muscular activity measuring device 150. The amplifier 130 may amplify the signal by $1.5*10^6$.

It is noted that the amplifier 130 may be optional is the strength from the sensor 210 is strong enough to process by the respiratory measuring device 140, the cardio measuring device 145, and the muscular activity measuring device 150.

It is noted that although FIG. 4 illustrates that the respiratory measuring device 140, the cardio measuring device 145, and the muscular activity measuring device 150 are connected in parallel, these devices can operate in a serial fashion.

It is further noted that although FIG. 4 illustrates that the respiratory measuring device 140, the cardio measuring device 145, and the muscular activity measuring device 150 are separate devices, the functions of these devices, as described below, may be realized by a processor executing an application, an application specific integrated circuit, and/or a combination of hardware, firmware, and/or software.

The respiratory measuring device 140 monitors the amplified signal from the amplifier 130 to detect signals representing respiration (breathe). An example of an amplified signal that shows respiration is FIG. 9.

As illustrated in FIG. 9, an amplified signal 600 represents a user (patient) using the compression device while resting or sleeping on their back. The respiratory measuring device 140 detects respiration (breathe) when the difference (610) between a signal peak and a signal minimum is greater than a predetermined threshold. For example, if the difference (610) between a signal peak and a signal minimum represents a difference greater than 0.1 mmHg or approximately 5 mV, respiration (breathe) is detected.

The cardio measuring device 145 monitors the amplified signal from the amplifier 130 to detect signals representing heart functions (pulse). An example of an amplified signal that shows heart functions (pulse) is FIG. 7.

As illustrated in FIG. 7, an amplified signal 500 represents a user (patient) using the compression device while resting or sleeping on their side (making it harder to detect respiration) or while holding their breathe. The cardio measuring device 145 detects heart functions (pulse) when the difference (510) between a signal peak and a signal minimum is greater than a predetermined threshold. For example, if the difference (510) between a signal peak and a signal minimum represents a difference greater than 0.1 mmHg or approximately 5 mV, a heart function (pulse) is detected.

The muscular activity measuring device 150 monitors the amplified signal from the amplifier 130 to detect signals representing muscular activity. An example of an amplified signal that shows muscular activity is FIG. 5.

As illustrated in FIG. 5, an amplified signal 400 represents a user (patient) using the compression device while engaging in muscular activity, such as walking, etc. The muscular activity measuring device 150 detects muscular activity when the difference (410) between a signal peak and a signal minimum is greater than a predetermined threshold. For example, if the difference (510) between a signal peak and a signal minimum represents a difference greater than 0.1 mmHg or approximately 5 mV, muscular activity is detected.

It is noted that when a user (patient) using the compression device is walking, the muscle generated signals would mask all other signals since the muscle generated signals are much stronger than the pulse or breathe signals.

It is further noted that a predetermined time interval may be required between measured signals; e.g., a two second interval between signals; to avoid or filter out signals associated with vibrations caused by a nearby electronic appliance.

It is also noted that the respiratory measuring device 140, the cardio measuring device 145, and the muscular activity measuring device 150, each contain sampling and/or filtering functionality to process the gross signal received from the amplifier 130.

For example, the respiratory measuring device 140 may include sampling and/or filtering functionality which would process the gross signal received from the amplifier 130 so that a periodic signal, having a cycle representative of the patient's normal respiration rate or a predetermined respiration rate, would be realized. This periodic signal, as illustrated in FIG. 9, can be further analyzed to determine the difference between a signal peak and a signal minimum (610) would be effective in detecting respiration. Such filtering and/or sampling techniques are well-known in the art.

Moreover, for example, the muscular activity measuring device 150 may include sampling and/or filtering functionality which would process the gross signal received from the amplifier 130 so that a periodic signal, having a cycle representative of the patient's normal pulse rate or a predetermined pulse rate, would be realized.

This periodic signal, as illustrated in FIG. 5, can be further analyzed to determine the difference between a signal peak and a signal minimum (410) would be effective in detecting muscular activity. Such filtering and/or sampling techniques are well-known in the art.

Lastly, for example, the cardio measuring device 145 may include sampling and/or filtering functionality which would process the gross signal received from the amplifier 130 so that a periodic signal, having a cycle representative of the patient's normal pulse rate or a predetermined pulse rate, would be realized. This periodic signal, as illustrated in FIG. 7, can be further analyzed to determine the difference between a signal peak and a signal minimum (510) would be effective in detecting cardio activity. Such filtering and/or sampling techniques are well-known in the art.

As illustrated in FIG. 4, the respiratory measuring device 140, the cardio measuring device 145, and the muscular activity measuring device 150 output the detection signals (positive signals indicating the measured activity) to the compliance device 155.

The compliance device 155 receives the various detection signals and determines if the user is in compliance with the prescribed usage of the compression device.

To determine compliance, the compliance device 155 determines if a predetermined number of detection signals are received within a predetermined window of time.

For example, the compliance device 155 may make a positive compliance determination if five positive detection signals are received during a five minute interval. More specifically, if the compliance device 155 receives five positive detection signals in a five minute window, the compliance device 155 determines that the user's utilization of the compression device is in compliance.

It is noted that the five positive detection signals may not be all from the same source (the respiratory measuring device 140, the cardio measuring device 145, or the muscular activity measuring device 150).

For example, the five detection signals can be all pulse detection signals, all breathe detection signals, or all muscular activity detection signals, or any combination thereof; e.g., two breathe detection signals, two pulse detection signals, and one muscular activity detection signal, etc.

It is noted that if only a single cuff is utilized in the therapeutic treatment, each detected positive detection signal may counted as two positive detection signal signals in the compliance analysis.

Figure 11:
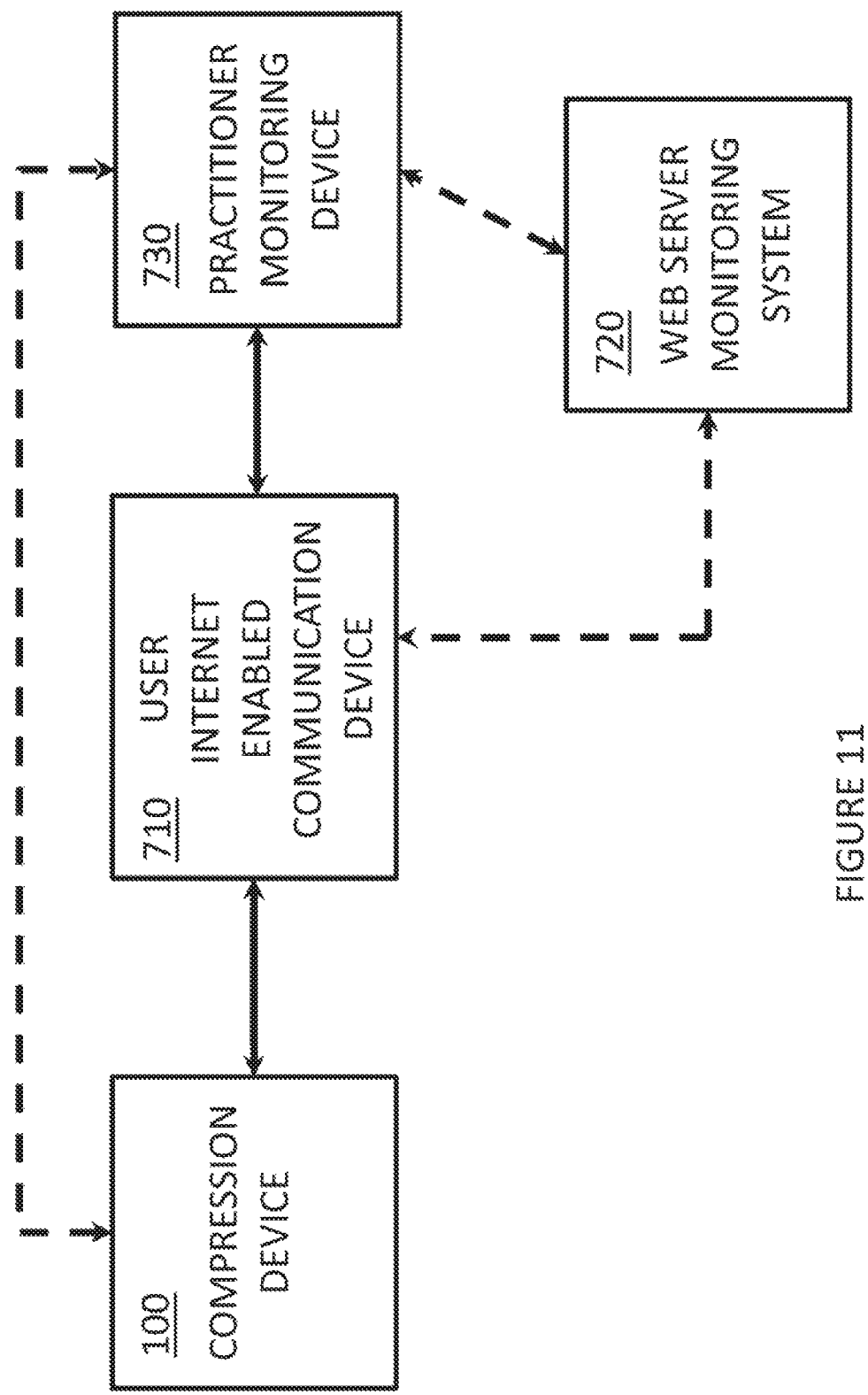
FIG. 11 is a schematic block diagram of communications between a compression device and a compliance monitoring system.

FIG. 11 illustrates a system for communicating the compliance information to a care-provider or medical practitioner.

As illustrated In FIG. 11, the compliance information generated by the compliance device associated with the compression device 100, discussed above with respect to FIGS. 3 and 4, can be communicated to a user internet enabled communication device 710, over a wired communication path or wireless communication path.

The user internet enabled communication device 710 may be a personal communication device that is internet enabled, a personal digital assistant device that is internet enabled, etc. An internet enabled device is a device that is in communication with a local area network and is able to communicate with other devices residing on the internet, or a device that has the functionality to connect directly to the internet, without relying upon a local area network, and is able to communicate with other devices residing on the internet.

As illustrated in FIG. 11, the user internet enabled communication device 710 may communicate over the internet to a medical practitioner (or care-provider) monitoring device 730 which registers and stores the compliance information. The medical practitioner (or care-provider) monitoring device 730 may be a personal communication device that is internet enabled, a personal digital assistant device that is internet enabled, a personal computer, a mobile computer, a tablet, etc.

The medical practitioner or care-provider may, through the medical practitioner (or care-provider) monitoring device 730, communicate back to the user (patient) instructions about usage of the compression device 100 if the user is not in compliance.

It is noted that, as illustrated in FIG. 11, the user internet enabled communication device 710 may communicate to a web server monitoring system 720 which registers and stores the compliance information. The web server monitoring system 720 may forward the compliance information to the medical practitioner (or care-provider) monitoring device 730 if intervention or instructions are needed.

The medical practitioner or care-provider may, through the medical practitioner (or care-provider) monitoring device 730, communicate back to the user (patient), through web server monitoring system 720, instructions about usage of the compression device 100 if the user is not in compliance.

Figure 12:
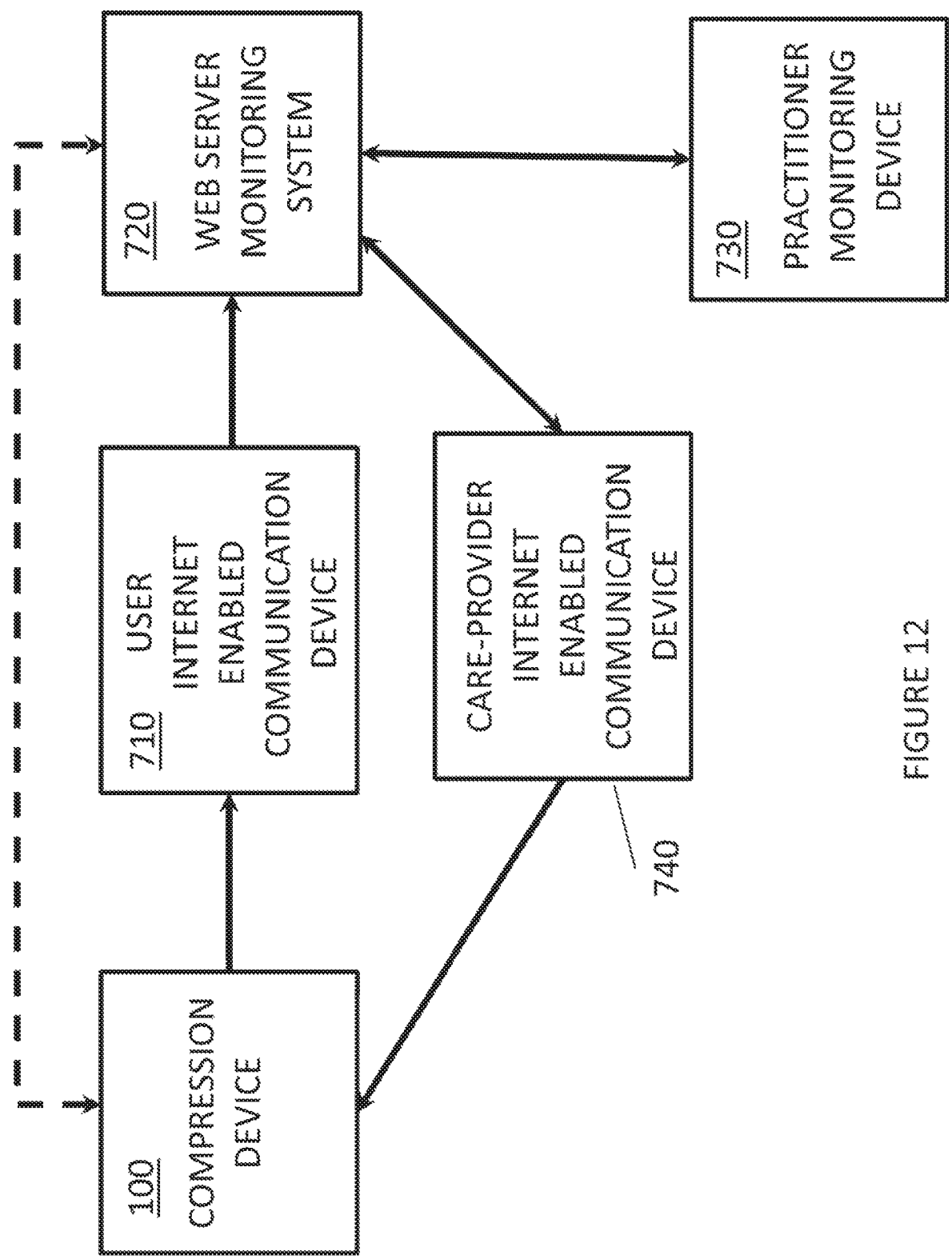
FIG. 12 is another schematic block diagram of communications between a compression device and a compliance monitoring system.

FIG. 12 illustrates another system for communicating the compliance information to a care-provider or medical practitioner.

As illustrated In FIG. 12, the compliance information generated by the compliance device associated with the compression device 100, discussed above with respect to FIGS. 3 and 4, can be communicated to a user internet enabled communication device 710, over a wired communication path or wireless communication path.

The user internet enabled communication device 710 may be a personal communication device that is internet enabled, a personal digital assistant device that is internet enabled, etc. An internet enabled device is a device that is in communication with a local area network and is able to communicate with other devices residing on the internet, or a device that has the functionality to connect directly to the internet, without relying upon a local area network, and is able to communicate with other devices residing on the internet.

As illustrated in FIG. 12, the user internet enabled communication device 710 may communicate to a web server monitoring system 720 which registers and stores the compliance information. The web server monitoring system 720 may forward the compliance information to the medical practitioner (or care-provider) monitoring device 730 if intervention or instructions are needed.

The medical practitioner (or care-provider) monitoring device 730 may be a personal communication device that is internet enabled, a personal digital assistant device that is internet enabled, a personal computer, a mobile computer, a tablet, etc.

The medical practitioner or care-provider may, through the medical practitioner (or care-provider) monitoring device 730, communicate back to a care-provider, through the web server monitoring system 720 and care-provider internet enabled communication device 740, about usage of the compression device 100 if the user is not in compliance.

The care-provider may, through the care-provider internet enabled communication device 740, communicate back to the user (patient), instructions about usage of the compression device 100 if the user is not in compliance.

It is noted that the communication between the various devices may be a push communication; e.g., the compression device 100 pushes out the compliance information, or a pull communication, e.g., the web server monitoring system 720 or the medical practitioner (or care-provider) monitoring device 730 request (or poll) the compliance information from the compression device 100.

It is further noted that the communication system discussed above can be utilized to lock or unlock the functionality of the compression device 100. For example, the web server monitoring system 720 or the medical practitioner (or care-provider) monitoring device 730 may generate an unlock code for the compression device 100. The unlock code can be communicated to the user internet enabled communication device 710. The unlock code could be either manually entered into the compression device 100 or communicated from the user internet enabled communication device 710 to the compression device 100.

It is further noted that the web server monitoring system 720 or the medical practitioner (or care-provider) monitoring device 730 may generate lock code for the compression device 100. The lock code can be communicated to the user internet enabled communication device 710. The lock code would then be automatically communicated from the user internet enabled communication device 710 to the compression device 100 to lock the device.

It is further noted that the compression device 100 may also monitor or detect other biological events and information associated with these biological events can be communicated to the medical practitioner or care-provider over the communication system of FIGS. 11 and 12.

Figure 13:
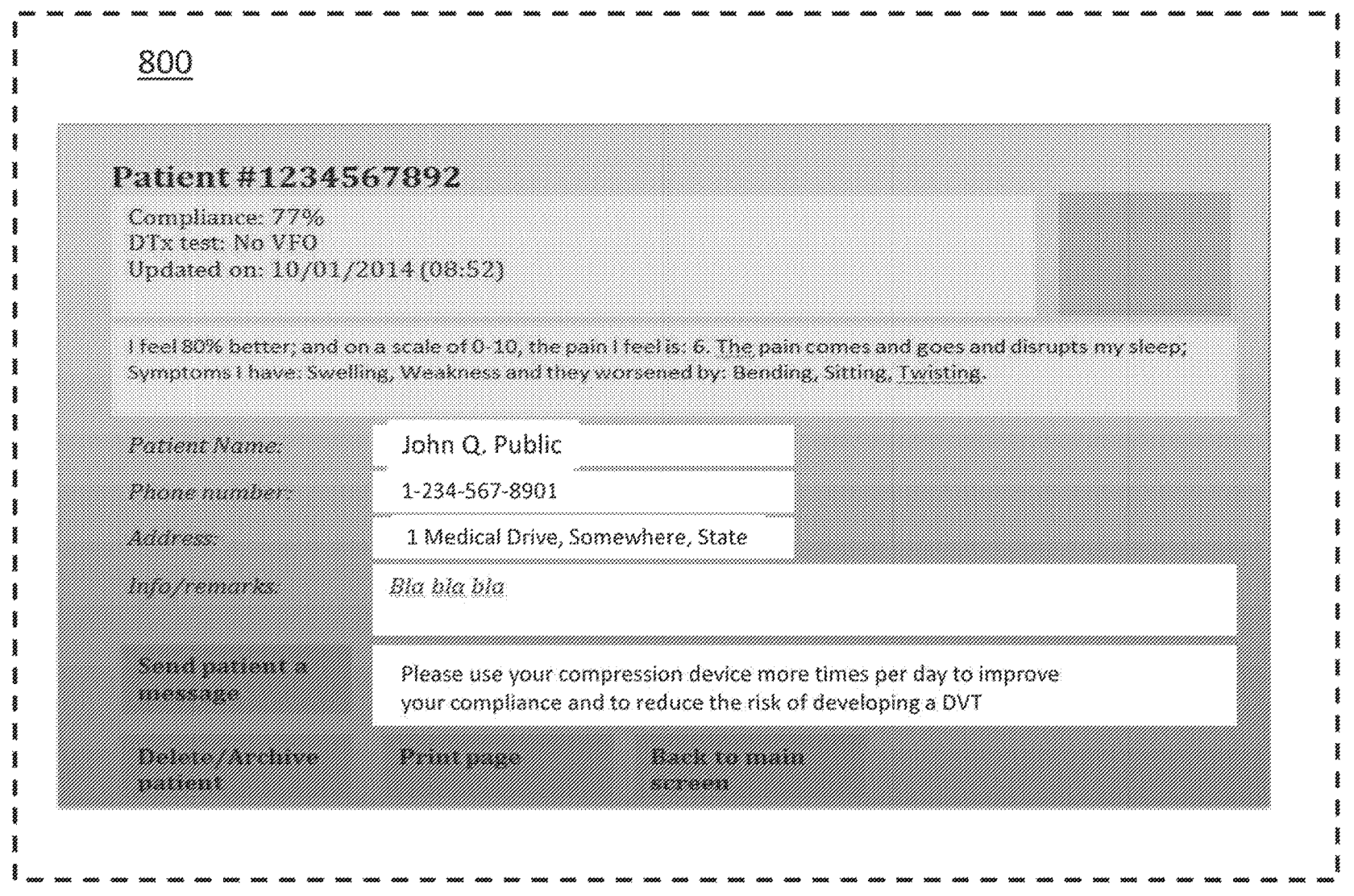

FIG. 13 illustrates an example of a display page on a display screen 800 which may be associated with medical practitioner (or care-provider) monitoring device 730 or care-provider internet enabled communication device 740.

As illustrated in FIG. 13, the display page may convey the patient's information, compliance information, patient's comments, etc. The display page may allow the medical practitioner or care-provider to send a message back to the patient, delete or archive the information, print the information, etc.

A system for determining a user's compliance with a prescribed therapeutic pneumatic compression treatment, comprise a pneumatic compression system for applying external pressure to a body limb. The pneumatic compression system includes a console, a pneumatic compression sleeve, pneumatically connected to the console, for applying compression to a body limb, and a pressure sensor. The pneumatic compression sleeve has a pneumatically fillable cell. The pressure sensor, pneumatically connected to the pneumatically fillable cell of the pneumatic compression sleeve, measures pneumatic pressure within the pneumatically fillable cell.

The console includes a respiratory measuring device operatively connected to the pressure sensor, a cardio measuring device operatively connected to the pressure sensor, a muscular activity measuring device operatively connected to the pressure sensor, and a compliance determining device operatively connected to the respiratory measuring device, the cardio measuring device, and the muscular activity measuring device.

The respiratory measuring device, based upon a pressure signal received from the pressure sensor, determines respiratory events associated with the user and generates a positive detection signal for each determined respiratory event associated with the user.

The cardio measuring device, based upon a pressure signal received from the pressure sensor, determines cardio events associated with the user and generates a positive detection signal for each determined cardio event associated with the user.

The muscular activity measuring device, based upon a pressure signal received from the pressure sensor, determines muscular activity events associated with the user and generates a positive detection signal for each determined muscular activity event associated with the user.

The compliance determining device determines a user's compliance with a prescribed therapeutic pneumatic compression treatment when the compliance determining device has received a predetermined number of positive detection signals within a predetermined time interval.

The pressure sensor may be located in the console.

The pressure sensor may be located in the pneumatic compression sleeve.

The compliance determining device may determine a user's compliance with a prescribed therapeutic pneumatic compression treatment when the compliance determining device has received five positive detection signals within the predetermined time interval.

The compliance determining device may determine a user's compliance with a prescribed therapeutic pneumatic compression treatment when the compliance determining device has received the predetermined number of positive detection signals within a five minute time interval.

The compliance determining device may determine a user's compliance with a prescribed therapeutic pneumatic compression treatment when the compliance determining device has received five positive detection signals within a five minute time interval.

The compliance determining device may determine a user's compliance with a prescribed therapeutic pneumatic compression treatment when the compliance determining device has received two positive detection signals from the respiratory measuring device, two positive detection signals from the cardio measuring device, and one positive detection signal from the muscular activity measuring device within a five minute time interval.

The positive detection signal may represent when a difference between a pressure signal peak and a pressure signal minimum is greater than a predetermined threshold.

The positive detection signal may represent when a difference between a measured pressure peak and a measured pressure minimum is greater than 0.1 mmHg.

The console may further includes an amplifier to amplify the pressure signal before the pressure signal is processed by the respiratory measuring device, the cardio measuring device, and the muscular activity measuring device.

A method for determining a user's compliance with a prescribed therapeutic pneumatic compression treatment comprises applying external pressure to a body limb using a pneumatic compression sleeve having a pneumatically fillable cell; measuring pneumatic pressure within the pneumatically fillable cell; generating a pressure signal corresponding to the measured pneumatic pressure; determining respiratory events associated with the user based upon the pressure signal; generating a positive detection signal for each determined respiratory event associated with the user; determining cardio events associated with the user based upon the pressure signal; generating a positive detection signal for each determined cardio event associated with the user; determining muscular activity events associated with the user based upon the pressure signal; generating a positive detection signal for each determined muscular activity event associated with the user; and determining a user's compliance with a prescribed therapeutic pneumatic compression treatment when a predetermined number of positive detection signals have been generated within a predetermined time interval.

A user's compliance with a prescribed therapeutic pneumatic compression treatment may be determined when five positive detection signals have been generated within the predetermined time interval.

A user's compliance with a prescribed therapeutic pneumatic compression treatment may be determined when the predetermined number of positive detection signals has been generated within a five minute time interval.

A user's compliance with a prescribed therapeutic pneumatic compression treatment may be determined when five positive detection signals has been generated within a five minute time interval.

A user's compliance with a prescribed therapeutic pneumatic compression treatment may be determined when two positive detection signals representing respiratory events, two positive detection signals representing cardio events, and one positive detection signal representing muscular activity events have been generated within a five minute time interval.

The positive detection signal may represent when a difference between a pressure signal peak and a pressure signal minimum is greater than a predetermined threshold.

The positive detection signal may represent when a difference between a measured pressure peak and a measured pressure minimum is greater than 0.1 mmHg.

The pressure signal may be amplified before the pressure signal is processed for event detection.

While various examples and embodiments have been shown and described, it will be appreciated by those skilled in the art that the spirit and scope of the embodiments are not limited to the specific description and drawings herein.

What is claimed is:

1. A method for determining a user's compliance with a prescribed therapeutic pneumatic compression treatment, comprising:
    applying external pressure to a body limb using a pneumatic compression sleeve, controlled by a pneumatic compression system, the pneumatic compression sleeve having a pneumatically fillable cell;
    measuring, using a pressure sensor, pneumatic pressure within the pneumatically fillable cell;
    generating, from the pressure sensor, a pressure signal corresponding to the measured pneumatic pressure;
    determining, on a processor, respiratory events associated with the user based upon the pressure signal;
    generating, on the processor, a positive detection signal for each determined respiratory event associated with the user;
    determining, on the processor, cardio events associated with the user based upon the pressure signal;
    generating, on the processor, a positive detection signal for each determined cardio event associated with the user;
    determining, on the processor, muscular activity events associated with the user based upon the pressure signal;
    generating, on the processor, a positive detection signal for each determined muscular activity event associated with the user; and
    determining, on the processor, a user's compliance with a prescribed therapeutic pneumatic compression treatment when a predetermined number of positive detection signals have been generated within a predetermined time interval.

2. The method as claimed in claim 1, wherein the user's compliance with a prescribed therapeutic pneumatic compression treatment is determined when five positive detection signals have been generated within said predetermined time interval.

3. The method as claimed in claim 1, wherein the user's compliance with a prescribed therapeutic pneumatic compression treatment is determined when the predetermined number of positive detection signals has been generated within a five minute time interval.

4. The method as claimed in claim 1, wherein the user's compliance with a prescribed therapeutic pneumatic compression treatment is determined when five positive detection signals has been generated within a five minute time interval.

5. The method as claimed in claim 1, wherein the user's compliance with a prescribed therapeutic pneumatic compression treatment is determined when two positive detection signals representing the respiratory events, two positive detection signals representing the cardio events, and one positive detection signal representing the muscular activity events have been generated within a five minute time interval.

6. The method as claimed in claim 1, wherein the positive detection signal represents when a difference between a pressure signal peak and a pressure signal minimum is greater than a predetermined threshold.

7. The method as claimed in claim 1, wherein the positive detection signal represents when a difference between a measured pressure peak and a measured pressure minimum is greater than 0.1 mmHg.

8. The method as claimed in claim 1, wherein the pressure signal is amplified before the pressure signal is processed for event detection.

9. A method for determining a user's compliance with a prescribed therapeutic pneumatic compression treatment, comprising:
   applying external pressure to a body limb using a pneumatic compression device;
   generating, using a pressure sensor, a pressure signal corresponding to a measured pneumatic pressure associated with the pneumatic compression device;
   monitoring, using a processor receiving the pressure signal from the pressure sensor, the measured pneumatic pressure to detect biological events associated with the user, the biological events detected when the difference between a signal peak and a signal minimum is greater than a predetermined threshold, wherein the biological events include respiratory events, cardio events, and muscular activity events determined from the pressure signal;
   generating, using the processor, a positive detection signal for each determined biological event associated with the user; and
   determining, using the processor, the user's compliance with a prescribed therapeutic pneumatic compression treatment when a predetermined number of positive detection signals have been generated within a predetermined time interval.

10. The method of claim 9, wherein the pneumatic compression device comprises a plurality of pneumatically fillable cells.

11. The method of claim 9, wherein the predetermined threshold is 0.1 mmHg.

12. The method of claim 9, wherein applying external pressure comprises applying cyclic sequential pressure to the body limb.

13. A method for determining a user's compliance with a prescribed therapeutic pneumatic compression treatment, comprising:
   applying external pressure to a body limb using a pneumatic compression device;
   measuring, using a pressure sensor, pneumatic pressure within a fillable cell of the pneumatic compression device;
   generating, from the pressure sensor, a pressure signal corresponding to the measured pneumatic pressure;
   determining, using a processor, biological events associated with the user based upon the pressure signal, the biological events including respiratory events, cardio events, and muscular activity events;
   generating, using a processor, a positive detection signal for each determined biological event associated with the user; and
   determining, using a processor, the user's compliance with a prescribed therapeutic pneumatic compression treatment, the determining based at least in part on the positive detection signal for each determined therapeutic event.

14. The method of claim 13, wherein determining the user's compliance with the prescribed therapeutic pneumatic compression treatment is performed when a predetermined number of positive detection signals have been generated.

15. The method of claim 13, wherein determining the user's compliance with the prescribed therapeutic pneumatic compression treatment is performed after a predetermined time interval.

16. The method of claim 13, wherein determining the user's compliance with the prescribed therapeutic pneumatic compression treatment is performed when a predetermined number of positive detection signals have been generated within a predetermined time interval.

17. The method of claim 13, wherein the pressure signal is amplified before the pressure signal is processed for event detection.

* * * * *